United States Patent [19]

Gekhman et al.

[11] 4,178,935

[45] Dec. 18, 1979

[54] METHOD AND APPARATUS FOR DISINTEGRATION OF URINARY CONCRETIONS

[76] Inventors: Boris S. Gekhman, ulitsa Parizhskoi kommuny, 22-B, kv. 24; Petr N. Vasilevsky, bulvar Druzhby narodov, 8, kv. 27; Jury G. Ediny, prospekt 40-letia Oktyabrya, 88, kv. 67; Ivan V. Parfinenko, ulitsa Kochubeevskaya, 12ª, kv. 1; Alfred M. Podgursky, Elektrotekhnichesky pereulok, 3, kv. 10, all of Kiev, U.S.S.R.

[21] Appl. No.: 817,787

[22] Filed: Jul. 21, 1977

[51] Int. Cl.² ............................................. A61B 17/00
[52] U.S. Cl. ................................................. 128/328
[58] Field of Search ............... 128/328, 24 A, 303.15, 128/4, 303 C, 7

[56] References Cited

U.S. PATENT DOCUMENTS

| 3,413,976 | 12/1968 | Roze .................................... 128/328 |
| 3,831,585 | 8/1974 | Brondy et al. .................. 128/328 X |

Primary Examiner—Henry J. Recla
Attorney, Agent, or Firm—Lackenbach, Lilling & Siegel

[57] ABSTRACT

A method and apparatus are provided for disintegrating urniary concretions by subjecting the urinary concretions to ultrasonic forces and electro-hydraulic impacts. For this purpose the apparatus comprises a milling cutter and a discharge arrester alternately inserted into the ureter through a catheter and provided with stops adapted to restrict the axial movement of the milling cutter and the discharge arrester inside the catheter. The method for disintegration of urinary concretions by means of said apparatus includes ultrasonic and electro-hydraulic actions carried out alternatively without withdrawing the catheter from the ureter to completely disintegrate the concretion during one session of treatment.

12 Claims, 11 Drawing Figures

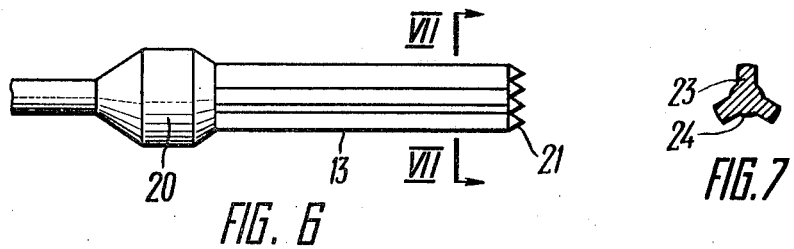
FIG. 6
FIG. 7
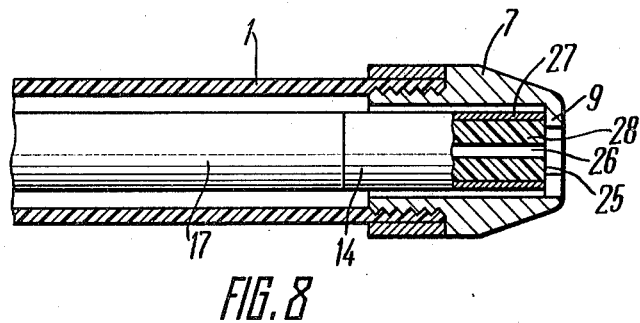
FIG. 8
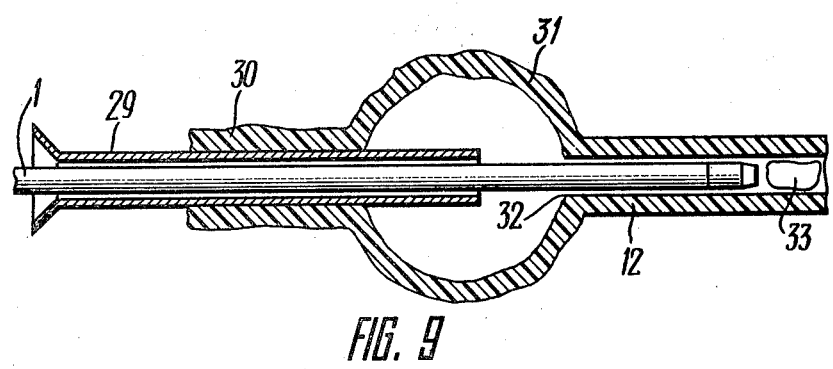
FIG. 9

METHOD AND APPARATUS FOR DISINTEGRATION OF URINARY CONCRETIONS

FIELD OF THE INVENTION

The present invention relates to methods and apparatus for disintegration of urinary concretions and may be used during internal treatment of urolithiasis.

DESCRIPTION OF THE PRIOR ART

As clinical experience has shown, the removal of urinary concretions is a very urgent and yet not sufficiently solved problem. If stones (concretions) are quite small (not more than 5mm) they may be removed from the urinary tract by means of conventional extractors, as is disclosed in U.S. Pat. No. 3,074,408. Such extractors comprise an expanding and contracting means and a stone-catching basket. The above expanding and contracting means and the basket are mounted on a tip of a catheter adapted to be passed cystoscopically through the urethra into the ureter. However, the use of these instruments even in experienced hands, may involve certain hazards of mechanical manipulation, since the expanding and contracting means and the basket of the extractor often cause the rupture of the ureter, the urethra and even the bladder. Furthermore, cases are known where the loop or the basket of the extractor with the concretion imprisoned therein cannot be passed out of the ureter, thereby necessitating an immediate surgical intervention. Further, stones which are quite large in some cases cannot be caught by the basket or loop, to say nothing of passing through the urinary tract.

Attempts have been made to take advantage of an electrohydraulic impact to disintegrate comparatively large concretions in the bladder and ureter. A device for electro-hydraulic disintegration of concretions comprises a discharge arrester mounted on the tip of the catheter and associated with a source of direct current. With the purpose of disintegrating the concretion, the ureter is first fed with a liquid, for instance, water, and then electrodes of the discharge arrester are coupled to the power source so as to set up a difference in electrical potential between the electrodes. The disruption of the discharge gap between the electrodes of the discharge arrester causes a hydraulic impact which crushes the stone. But the application of such a device is not always advisable. In particular, stones without hollows, depressions or projections are difficult to break up. Furthermore, the use of the discharge arrester during stone disintegration in a curved ureter may cause scalding and even piercing thereof.

At present extensive use for bloodless removal of concretions is made of ultrasonic methods and apparatus. The idea of vibratory impact machining of urinary concretions is not new. Specifically, known in the art is a great number of impact machining techniques adapted to disintegrate concretions by means of vibrations in the ultrasonic range of frequencies. Methods of disintegrating concretions have proved to be advantageous, in which a catheter is first passed cystoscopically into the ureter and then a milling cutter is passed through the internal duct of the catheter to the side of the stone. An ultrasonic transducer is attached to the operating element and energized, thereby providing for ultrasonic vibrations which act upon the concretion and cause its fragmentation, as is disclosed in U.S. Pat. No. 3,830,240.

An apparatus for disintegration of urinary concretions, as described hereinabove, comprises a catheter with a coupling member passing therethrough in the internal axial duct, carrying an operating element on one its end, and associated by its other end with an ultrasonic transducer. The catheter is a flexible tube and the operative element is a milling cutter which may be of various configurations according to the shape, location and composition of the concretion. The coupling member is a resilient wave guide adapted to transmit longitudinal and transverse vibrations from the ultrasonic transducer to the operating element (milling cutter).

The evident advantage of this method over prior art is that even rather large calcareous concretions can be fragmented in under 60 sec., i.e. before excessive heat generation along the wave guide seriously affects the organism. But despite the above advantage, the application of this method does not always bring about the desired success. Specifically, in some cases only small hollows can be made on the surface of the calculus, whereas the increase of time of the vibratory action on the concretion may give rise to complications, such as a breakage of the wave guide and loss of the milling cutter in the ureter. The removal of such a foreign body from the ureter through the catheter involves serious difficulties and often necessitates an immediate surgical intervention. It should be noted, that repeated attempts by the doctor to use vibrations on the concretion may be carried out not earlier than several days after the failure. This is due to the fact that after the removal of the catheter the meatus of the urinary tract is severely irritated, and it is extremely difficult to insert the catheter again, even through the intermediary of a cystoscope.

SUMMARY OF THE INVENTION

The principal object of the present invention is to provide an improved apparatus for disintegration of urinary concretions which assures reliable holding of an operating element in place, thus excluding the possibility of accidental loss of said operating element, and allows for the integral action on the concretion by ultrasonic vibrations and an electrohydraulic impact.

Another object of the present invention is to provide an apparatus which combines ultrasonic and electrohydraulic action on the concretions and which is at the same time safe in operation and capable of crushing large concretions in the ureter.

One more object of the present invention is to prevent losses of the operating element either (a milling cutter or a discharge arrester) if the coupling member gets broken.

Yet another object of the present invention is the provision of an apparatus which prevents contact between the bare surface of the discharge arrester and the wall of the ureter, and at the same time makes it possible to supply liquid for an electro-hydraulic impact to be produced and for rinsing.

Another object of the present invention is to provide an apparatus which permits substantial crushing of concretions.

An additional object of the present invention is to improve the reliability of the apparatus in operation and diminish the danger of clogging the liquid supplying ducts with fragments of the concretion being crushed.

One more object of the present invention is to provide for a directed vibratory action on the concretion.

One more important object of the present invention is to provide an apparatus which with a minimum power input assures a sufficiently destructive electro-hydraulic effect.

Another essential object of the present invention is to provide a method for disintegration of urinary concretions with the aid of the proposed apparatus which makes it possible to carry out series of ultrasonic and electro-hydraulic actions on the concretion during one treatment procedure.

Still another object of the present invention is to provide a method for disintegration of urinary concretions which are large in size.

An additional object of the present invention is to provide a method of disintegration of urinary concretions which diminishes the danger of inflammation of the ureter walls.

These and other objects are achieved by an apparatus for disintegration of urinary concretions comprising a catheter adapted to be inserted into the ureter as well as an operating element intended to act upon the concretion with the purpose of fragmentation thereof and powered through a coupling member disposed inside the catheter. According to the invention, the catheter tip to be inserted into the ureter is provided with a bushing mounted coaxially with the catheter tip. The bushing comprises an inwardly projecting annular lip having longitudinal through ducts adapted for the supply of liquid to the region of the concretion. The operating element is provided with a bearing surface interacting with the lip inside the bushing.

The distinguishing advantages of the proposed apparatus over the prior art are that it assures a combined action upon the concretion by ultrasonic vibrations and electro-hydraulic impacts and at the same time practically excludes mechanical or electrical damages of the ureter wall. The bushing annular lip by interacting with the bearing surfaces of the milling cutter and of the discharge arrester prevents the milling cutter and the discharge arrester from being lost in the ureter if the coupling member gets broken (wire burns out), and prevents contact between the bare surface of the discharge arrester and the ureter wall. At the same time it provides for the supply of liquid during electrohydraulic impacts and rinsing.

The objects of the invention are more efficiently achieved when the bushing and the lip thereof are shaped and sized so as to permit alternate mounting as the operating element of a milling cutter and a discharge arrester each being provided with a coupling member of its own to be linked to and powered from an ultrasonic transducer and an electric pulse generator, respectively.

The objects of the invention are also achieved due to the fact that the bearing surface of the milling cutter is provided with a thickened portion on its non-working end, the diameter of this thickened portion being larger than the internal diameter of the annular lip. The milling cutter of such a design is capable of crushing concretions a comparatively greater amount without stopping against the annular lip.

It is expedient that the annular lip should be provided with longitudinal slots serving as ducts for the supply of liquid to the region of the concretion when the discharge arrester is being inserted into the bushing. Such an embodiment of the invention best meets the engineering requirements. Furthermore, such an arrangement of the ducts practically excludes the possibility of clogging them by fragments of the concretion.

According to one embodiment of the present invention, the milling cutter is provided with longitudinal projections and depressions on its lateral surface, said projections and depressions extending from the thickened portion on the non-working end towards the working end and fitting the slots and projections of the annular lip. Such an embodiment is best suited for directed vibrations acting upon the concretion.

Preferably, the external diameter of the discharge arrester should be smaller than the internal diameter of the bushing but larger than the internal diameter of the annular lip to assure stopping of the butt-end of the discharge arrester against the annular lip.

The most effective electro-hydraulic disintegration of the concretion has been carried out with an embodiment of the apparatus, wherein the thickness of the annular lip of the bushing is more than 1/6, but less than $\frac{1}{3}$, of the external diameter of the bushing.

These and other objects of the present invention are achieved by a method for disintegration of urinary concretion consisting of inserting the catheter into the ureter until the bushing end of the catheter rests against the concretion, passing of the operating element through the catheter and crushing the concretion. According to the invention, the concretion is initially acted upon by the milling cutter set into vibration and then, after substitution of the milling cutter by the discharge arrester without withdrawing the catheter from the ureter and after feeding the ureter with liquid, the concretion is acted upon by a hydraulic impact, the discharge arrester being introduced until its butt-end rests against the annular lip of the bushing. The principle advantage of this method for disintegration of urinary concretion is that even concretions which are large in size can be crushed during one treatment by changing the type of destructive action. The efficiency of such crushing is due to the fact that the ultrasonic element makes it possible to create hollows, channels and irregularities which, when acted upon by an electrohydraulic impact, contribute to the appearance of cracks and thereby to intensive crushing of the concretion. The interval between the ultrasonic action and electrohydraulic impact depends on the period of time necessary to withdraw the milling cutter from and to insert the discharge arrester into the catheter.

When crushing large concretions, it is expedient to carry out alternate actions by ultrasonic vibrations and electro-hydraulic impacts repeatedly without the withdrawal of the catheter from the urether until the concretion is crushed completely.

To prevent the inflammation of the ureter walls, it is advisable to inject drugs into the ureter through the internal duct of the catheter and the bushing after the concretion has been crushed.

BRIEF DESCRIPTION OF THE DRAWINGS

These and other objects, purposes and advantages of the invention will become apparent from a consideration of the following description and the accompanying drawings in which:

FIG. 6 is a longitudinal view of an embodiment of a milling cutter with longitudinal projections and depressions for a directed ultrasonic action upon the concretion, according to the invention;

FIG. 7 is a cross-sectional view taken along line VII—VII of FIG. 6;

FIG. 8 is a longitudinal sectional view of the catheter bushing with the discharge arrester inserted therein;

FIG. 9 is a longitudinal sectional view illustrating the catheter being passed cystoscopically into the ureter for disintegration of urinary concretions, according to the invention;

Figure 1:
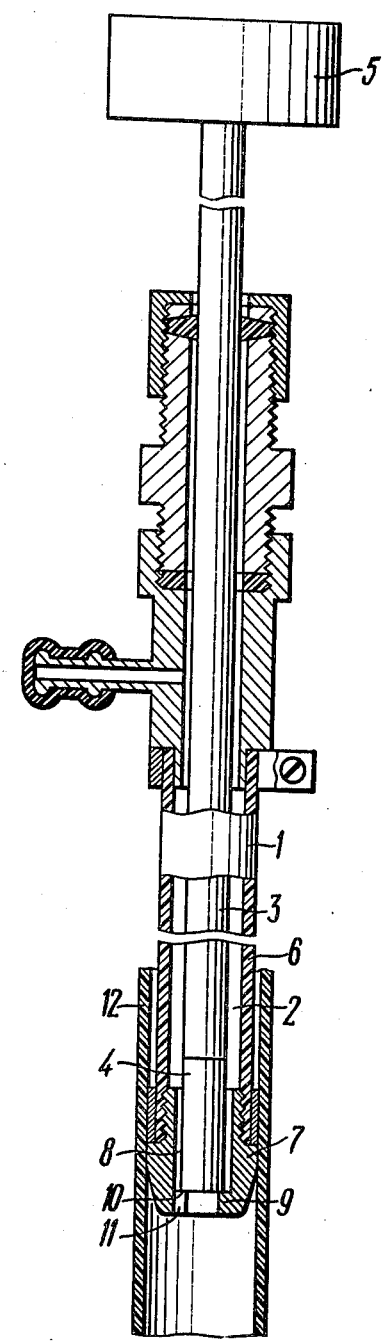
FIG. 1 is a sectional view of the apparatus for disintegration of urinary concretions, according to the invention.

Reference is now made to FIG. 1, which shows an apparatus for disintegration of urinary concretions comprising a catheter having an internal axial duct 2 and a coupling member 3 inserted in the axial duct 2. The coupling member 3 is provided with an operating element 4 on one end, its other being connected to a power pulse generator 5. The catheter 1 is a resilient tube 6 made of elastic material. The tip of the tube 6 of the catheter 1 is provided with a bushing 7 mounted coaxially therewith and having a centrally located through internal duct 8 and an inwardly projecting annular lip 9, according to the invention. The operating element 4 is provided with a bearing surface 10 which interacts with the annular lip 9 of the bushing 7 for limiting the axial movement of the operating element, according to the invention. The annular lip is provided with longitudinal through ducts 11 which are parallel to the axis of the bushing and assure the supply of liquid to the region of the concretion when the catheter is being inserted into the ureter 12.

Figure 2:
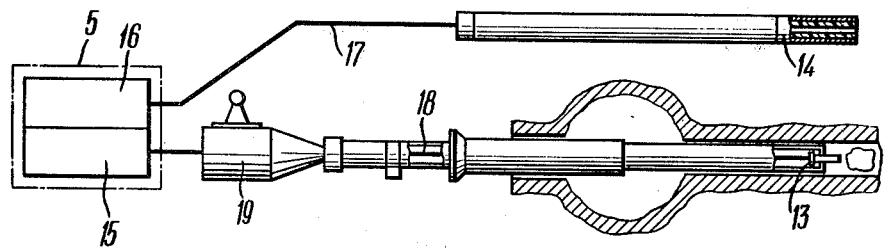
FIG. 2 is a longitudinal view, partly in section, of an alternative embodiment of the apparatus, wherein the interchangeable operating element provides for alternate actions upon the concretions, both ultrasonic and electro-hydraulic, according to the invention.

Reference is now made to FIG. 2, which shows the preferred embodiment of the apparatus, according to the invention. This embodiment provides for a design of the bushing which allows for alternate positioning, as the operating element 4, of a milling cutter 13 and a discharge arrester 14. The power pulse generator 5 comprises an ultrasonic transducer 15 and an electrical pulse generator 16. Each of the interchangeable operating elements is connected to a respective unit of the power pulse generator 5 through a coupling member of its own, according to the invention. In particular, the coupling member 3 of the discharge arrester 14 is made of two insulated from each other coaxial conductors 17 linking said discharge arrester to the electrical pulse generator 16 of the power pulse generator 5. The coupling member 3 of the milling cutter 13 is a wire 18 made, for instance, of steel which links the milling cutter 13 to the ultrasonic transducer 15 of the power pulse generator 5. The linking member 18 is coupled to the milling cutter 13, the length of the linking member being controlled by an adjusting device 19 which has a graduated circle with an indicator panel to provide for close control over the axial movement of the milling cutter 13.

Figure 3:
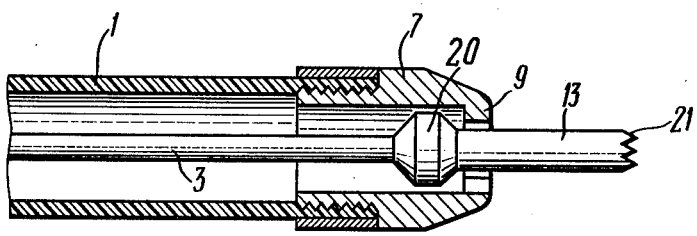
FIG. 3 is a longitudinal, sectional view illustrating the operating element as a milling cutter inserted into the bushing of the catheter for ultrasonic fragmentation of the concretion, according to the invention.

Reference is now made to FIG. 3, which shows an operating element 4, made as a milling cutter 13, inserted into the bushing 7 of the catheter 1. According to the invention, the milling cutter is provided with a thickened portion 20 on the non-working end and teeth 21 on the butt-end of the working end. The diameter of the thickened portion 20 is smaller than the internal diameter of the bushing 7, but larger than the internal diameter of the annular lip 9 which prevents loss of said milling cutter 13 in the ureter 12 if the coupling member 3 breaks during the process of disintegration of the concretion. The diameter of the working end of the milling cutter is smaller than the internal diameter of the annular lip 9 of the bushing 7 which permits to push forward the working end from said bushing 7 until the teeth 21 of said working end come into contact with the concretion.

Figure 4:
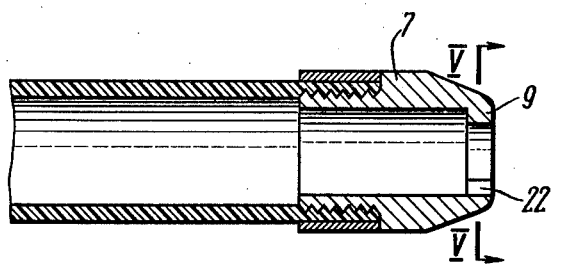
FIG. 4 is a longitudinal sectional view of an embodiment of the catheter bushing provided with longitudinal ducts in the annular lip, according to the invention.
Figure 5:
FIG. 5 is a cross-sectional view taken along the line V—V of FIG. 4, according to the invention.

Reference is now made to FIG. 4, which shows an alternative embodiment of the bushing 7, according to the invention. According to this embodiment, the annular lip 9 is provided with longitudinal slots 22, also illustrated in FIG. 5, said slots serving as longitudinal ducts for the supply of liquid to the region of the concretion. In this case, it is possible to apply the alternative embodiment of the milling cutter 13 shown in FIGS. 6 and 7. Preferably such an embodiment should be used during a directed ultrasonic vibratory action upon the concretion. According to this embodiment, the milling cutter 13 is provided on its lateral surface with longitudinal projections 23 and depressions 24 extending axially from the thickened portion 20 to the teeth 21 of the working end. The cross-section of the projections 23 and depressions 24 of the milling cutter 13 correspond to that of the longitudinal slots 22 disposed in the annular lip 9 of the bushing 7. When the working end of such a milling cutter is being inserted into the opening formed by the annular lip 9, the milling cutter can move only axially, thereby providing for directed action by ultrasonic vibrations upon the concretion.

Reference is now made to FIG. 8, which shows the bushing 7 of the catheter with the discharge arrester 14 inserted into said bushing. A butt-end 25 of the working end of the discharge arrester 14 serves in this case as a bearing surface of the discharge arrester 14. Since the diameter of said discharge arrester 14 is smaller than the internal diameter of the bushing 7, but larger than the internal diameter of the annular lip 9, the possibility of losing the discharge arrester in the ureter, if the wire 17 of the discharge arrester breaks or burns out, is eliminated. Also, for this reason, the bare working end of the discharge arrester 14 cannot come into contact with the walls of the ureter 12 and damage them during the supply of electric pulses. The discharge arrester 14 incorporates a centrally disposed internal electrode 26 and an external tubular electrode 27, positioned coaxial therewith. The gap between the electrodes 26 and 27 is filled with an electrically insulating material 28. According to the invention, the length of the annular lip 9 of the bushing 7 in its axial direction is more than 1/6 but less than ⅓ of the external diameter of the bushing. When such parameters are adhered to, the proposed apparatus with its comparatively small power capacity is capable of crushing large concretions.

The above described apparatus is used together with a cystoscope 29 which is inserted through a urethra 30 into a bladder 31 to assure a visual insertion of the catheter 1 into a meatus 32 of the ureter 12, as is shown in FIG. 9.

The method for disintegration of urinary concretions by means of the proposed apparatus will become apparent to those skilled in the art upon reference to the accompanying description of the mode of operation of the apparatus.

The proposed apparatus for disintegration of urinary concretions is used as follows.

Figure 10:
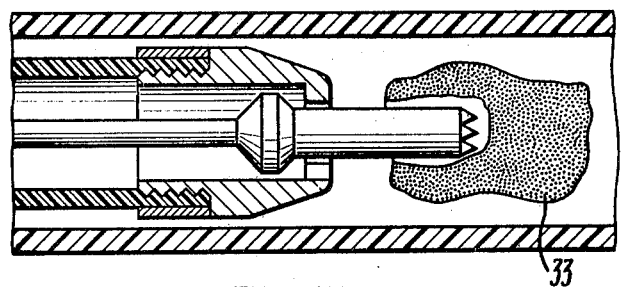
FIG. 10 is a longitudinal, sectional view at the moment of the ultrasonic action upon the concretion, according to the invention.
Figure 11:
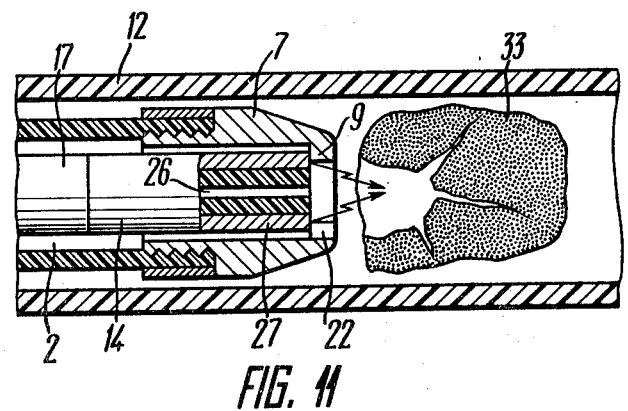
FIG. 11 is a longitudinal, sectional view during the second stage of complete fragmentation of the concretion by an electro-hydraulic impact, according to the invention.

The catheter 1 is passed cystoscopically into the meatus 32 of the ureter 12 and pushed forward until the end of the bushing 7 comes into contact with the concretion 33. Then the milling cutter 13 is inserted into the catheter and passed through the internal axial duct 2 thereof until the teeth 21 make contact with the concretion 33. At this point with contact assured the ultrasonic transducer 15 is energized, thereby setting the milling cutter 13 into longitudinal and transverse vibrations. By means of the adjusting device 19 the milling cutter 13 is moved forward boring the concretion 33 and making hollows or flutes therein, as is illustrated in FIG. 10. Then the ultrasonic transducer 15 is deenergized and, with the catheter 1 in the ureter 12, the milling cutter 13 with the coupling member 18 is withdrawn from the internal axial duct 2. The discharge arrester 14 is now inserted into the catheter until its butt-end rests against the annular lip 9. A liquid is supplied into the ureter 12 to the concretion 33 through the internal axial duct 2 of the catheter 1 and through the longitudinal slots 22 of the bushing 7. Distilled water may be used as such a liquid. Now the electrical pulse generator is energized and electrical current is supplied to the electrodes 26 and 27. At this point a disruptive discharge takes place in the liquid between the electrodes 26 and 27, thereby providing for a hydraulic impact acting upon the concretion 33. Because of the action of the hydraulic impact, the concretion is intensively broken up, mainly in the area where the hollows, flutes and irregularities have been previously formed by the milling cutter 13, as illustrated in FIG. 11. In most cases there is no need to repeat the above described sessions. However, if the concretion is large in size and difficult to crush completely, the sessions of alternate ultrasonic and electro-hydraulic actions are carried out repeatedly without withdrawing the catheter 1 from the ureter 12 until the concretion is crushed completely. After the concretion 33 has been crushed completely, the ureter 12 is fed with drugs injected through the internal duct of the catheter 1 and the internal duct 8 of the bushing 7 to prevent the inflammation of the walls of the ureter 12. Insertion of the catheter 1, milling cutter 13 and the discharge arrester 14 as well as fragmentation of urinary concretions are carried out under visual control which is conducted by means of an X-ray and TV installation.

The proposed apparatus may be used not only as described above. In particular, when urinary concretions in the bladder are to be crushed, only one type of action, electro-hydraulic or ultrasonic may be taken advantage of, for which purpose either the milling cutter 13 or the discharge arrester 14 is inserted into the catheter 1. Also, it is not always necessary to act upon the concretion by the combined action in the ureter. If the concretion has been crushed completely after the session of ultrasonic action, there is no need to make use of electrohydraulic action.

The distinguishing advantages of the present invention over the prior art reside in that it assures a combined action upon the concretion by ultrasonic vibrations and electro-hydraulic impacts and at the same time practically excludes mechanical or electrical damages of the ureter wall. Even concretions which are large in size can be crushed during one session of treatment, the duration of the session depending upon the duration of the ultrasonic and electro-hydraulic action as well as the period of time necessary to change the operating element (10–15 sec.).

From the foregoing, it will be seen that several objects, as well as numerous others have been obtained by the present invention. Accordingly, it is intended that this disclosure be taken as illustrative only since many changes, modifications and embodiments may be made without departing from the concept and intent.

We claim:

1. An apparatus for disintegration of urinary concretions comprising:

a catheter for insertion into the ureter;

a bushing having an axial bore coaxially mounted on one end of said catheter, having an inwardly projecting annular lip, said lip defining an axial bore smaller than the axial bore of said bushing and being provided with longitudinal through ducts extending through said lip for the supply of liquid to the region of the concretion;

an operating element within said catheter adapted to act upon the concretion and provided with a bearing surface adjacent said lip having a cross section larger than the axial bore defined by said lip, said bearing surface interacting with said lip inside said bushing for restriction of axial movement of said operating element from said bushing; and a coupling member supporting said operating element on one end, means connected to said coupling member on the opposite end for transmitting power to said operating element via said coupling member to activate it, said coupling member being coaxially disposed in said catheter; and wherein said bushing and the lip thereof are shaped and sized to permit alternate mounting of a milling cutter and a discharge arrester to be used as said operating element.

2. An apparatus according to claim 1 wherein said transmitting power means is a power pulse generator.

3. An apparatus according to claim 2, wherein said coupling member of said milling cutter includes an adjusting device for axial displacement of said milling cutter, said transmitting power generator having an ultrasonic transducer, and said coupling member is connected to an ultrasonic transducer of said power pulse generator, which powers said milling cutter.

4. An apparatus according to claim 2, wherein said coupling member of said discharge arrester includes two conductors insulated from each other, said power transmitting means includes a power pulse generator having an electric pulse generator, and said coupling member is connected to an electric pulse generator of said power pulse generator, which powers said discharge arrester.

5. An apparatus according to claim 1, wherein the operating element having said bearing surface is a milling cutter having a thickened portion with a diameter smaller than the internal diameter of the bushing but larger than the internal diameter of the annular lip.

6. An apparatus according to claim 1 wherein the annular lip is provided with longitudinal slots serving as said longitudinal ducts to supply liquid to the region of the concretion during passing of the discharge arrester into the bushing.

7. An apparatus according to claim 6, wherein the operating element is a milling cutter and is provided on a lateral surface with longitudinal projections and depressions extending from a thickened portion of a non-working end to the working end and having a cross-section which corresponds to that of the longitudinal slots of the bushing lip.

8. An apparatus according to claim 1, wherein the operating element is a discharge arrester having an external diameter smaller than the diameter of the bushing but larger than the internal diameter of the annular lip to prevent movement of a butt-end of the discharge arrester past the annular lip.

9. An apparatus according to claim 1, wherein the length of the annular lip in its axial direction is larger than 1/6 but smaller than ⅓ of the external diameter of the bushing.

10. A method of disintegration of urinary concretions comprising the following steps:
   inserting a catheter into the ureter until the end of the catheter bushing comes into contact with the concretion;
   inserting a milling cutter into the catheter by means of a coupling member until a working end of the milling cutter is disposed against the concretion;
   setting the milling cutter into longitudinal and transverse vibratory motion by means of an ultrasonic transducer and the coupling member to form depressions, flutes and other irregularities in the concretion;
   substituting a discharge arrester for the milling cutter inside the catheter, said substitution being carried out by withdrawing said milling cutter from said catheter and then passing the discharge arrester into the catheter until a butt-end of said discharge arrester is disposed against a lip of an internal duct of the bushing;
   supplying liquid through the internal duct of the catheter and longitudinal ducts of the bushing lip into the ureter and to the region of the concretion; and
   supplying direct current through a coupling member to the discharge arrester to act upon the concretion by an electro-hydraulic impact for fragmentation of said concretion.

11. A method according to clam 10, wherein alternate action upon the concretion by means of ultrasonic vibrations and electro-hydraulic impacts is carried out repeatedly without removing the catheter from the ureter until the concretion is crushed completely.

12. A method according to claim 10, further comprising the step of, after the disintegration of the concretion, introducing liquid drugs into the ureter through the internal duct of the catheter and bushing to prevent the inflammation of the ureter.

* * * * *